United States Patent [19]
Ramon et al.

[11] Patent Number: 5,170,784
[45] Date of Patent: Dec. 15, 1992

[54] LEADLESS MAGNETIC CARDIAC PACEMAKER

[76] Inventors: Ceon Ramon, 3845 NE. 86th St., Seattle, Wash. 98115; Gust H. Bardy, 2512 Crestmont West, Seattle, Wash. 98199

[21] Appl. No.: 618,696

[22] Filed: Nov. 27, 1990

[51] Int. Cl.⁵ .............................................. A61N 2/02
[52] U.S. Cl. .................. 128/419 PG; 600/14; 600/9
[58] Field of Search ........ 128/419 PG, 419 D, 419 F; 600/9, 13, 14, 15

[56] References Cited

U.S. PATENT DOCUMENTS

| | | | |
|---|---|---|---|
| 3,683,934 | 8/1972 | Bukowiecki et al. | 128/419 PG |
| 3,893,462 | 7/1975 | Manning | 600/13 |
| 3,915,151 | 10/1975 | Kraus | 600/13 |
| 4,056,097 | 11/1977 | Maass | 128/419 D |
| 4,723,536 | 2/1988 | Rauscher et al. | 600/14 |
| 5,066,272 | 11/1991 | Eaton et al. | 600/9 |

FOREIGN PATENT DOCUMENTS

| | | | |
|---|---|---|---|
| 3904254 | 9/1990 | Fed. Rep. of Germany | 128/419 D |
| 0665918 | 6/1979 | U.S.S.R. | 600/9 |
| 1537276 | 1/1990 | U.S.S.R. | 600/9 |

Primary Examiner—Kyle L. Howell
Assistant Examiner—Kennedy J. Schaetzle
Attorney, Agent, or Firm—Thomas R. Vigil

[57] ABSTRACT

The magnetic cardiac pacemaker utilizes bisphasic pulses of mixed frequencies and waveforms that are applied to a field coil to generate magnetic pulses of relatively low intensity (less than 200 Gauss) without the use of leads. The device can be worn externally on the chest near the heart to enable the magnetic field to penetrate the body and control the heart muscle as a non-invasive cardiac pacemaker or it can be inserted subcutaneously as a permanent non-lead system cardiac pacemaker.

22 Claims, 6 Drawing Sheets

LEADLESS MAGNETIC CARDIAC PACEMAKER

BACKGROUND OF THE INVENTION

1. Field of the Invention

The present invention relates to an apparatus and method for controlling the heart rhythm. More particularly, the invention relates to a magnetic pacemaker or stimulator of the heart capable of pacing the heart without the need for pacemaker leads. More particularly, the invention relates to a pacemaker device in which biphasic pulses of mixed frequencies generate a magnetic field of relatively low density (less than 200 Gauss) capable of stimulating the heart without contacting the heart muscle directly or with the aid of a transvenous lead.

2. Description of the Related Art Including Information Disclosed Under 37 CFR Sections 1.97–1.99

In medicine, electrical impulses are often used to stimulate the heart. Electrical depolarization of the heart has for over 30 years formed the basis for cardiac pacemakers that are used to control the heart rate when the normal intrinsic cardiac pacemaker fails.

To date, all known cardiac pacemakers both implantable and external non-implantable ones use electric pulse stimulation. In the case of permanently implanted pacemakers, the pacemaker is inserted under the skin and the leads (typically silicone or polyurethane coated cables) are inserted into the pacemaker to connect the power source to the heart via the subclavian venous system and the right ventricle.

Numerous problems are associated with implantable pacemakers, with the most notable source of difficulties being associated with the need for surgery to implant the leads into the veins and into the heart. Thus, a substantial advantage would be made available to patients if one were able to pace the heart without using an electrode.

In an effort to remove the need for an endocardial or epicardial lead system, we have developed a unique method using magnetic pulses for non contact cardiac pacing. Previous efforts in the field has been limited to high intensity magnetic field strength, an impractical energy source for implantable pacemakers or even external transthoracic pacemakers. See Irwin, Don D., et al.. "Stimulation of Cardiac Muscle by a Time-Varying Magnetic Field," *IEEE Trans. on Mag.*, Vol. Mag-6, No. 2, June 1970, pages 321-2. That earlier research used magnetic fields to induce an electric field in the cardiac cells but required a magnetic field on the order of 1 kilogauss or more producing a very large bulk effect to simulate the equivalent of an implanted electrode. More importantly, the use of such a strong electromagnetic field can have the serious negative side effect of heating and destroying surrounding tissue as well as the heart itself.

The present invention overcomes the disadvantages of known devices by using a low or medium strength magnetic field (less than 200 Gauss) to directly trigger cell function. The device producing the fields can be completely external to the body or can be placed on or under the skin and does not have any known adverse side effects. It also has the potential for miniaturization and insertion under the skin as a permanently implantable pacemaker without the need for a lead system.

SUMMARY OF THE INVENTION

As will be described in more detail below, the present invention comprises either a non-invasive temporary or a subcutaneous implantable permanent cardiac pacemaker without having a venous lead system having at least two function generators for producing discrete electrical signals, each having its own waveform and frequency.

If desired, two function generators and delay timer can be replaced by a computer chip producing the same wave forms. These signals are mixed, amplified, and then applied to a field coil for generating pulsed magnetic field signals. The device is contained in a housing that is essentially transparent to magnetic fields to permit the device to be worn outside the body or subcutaneously and the magnetic field generated by it to be directed into the thorax to the heart.

DESCRIPTION OF THE PREFERRED EMBODIMENT

Figure 1:
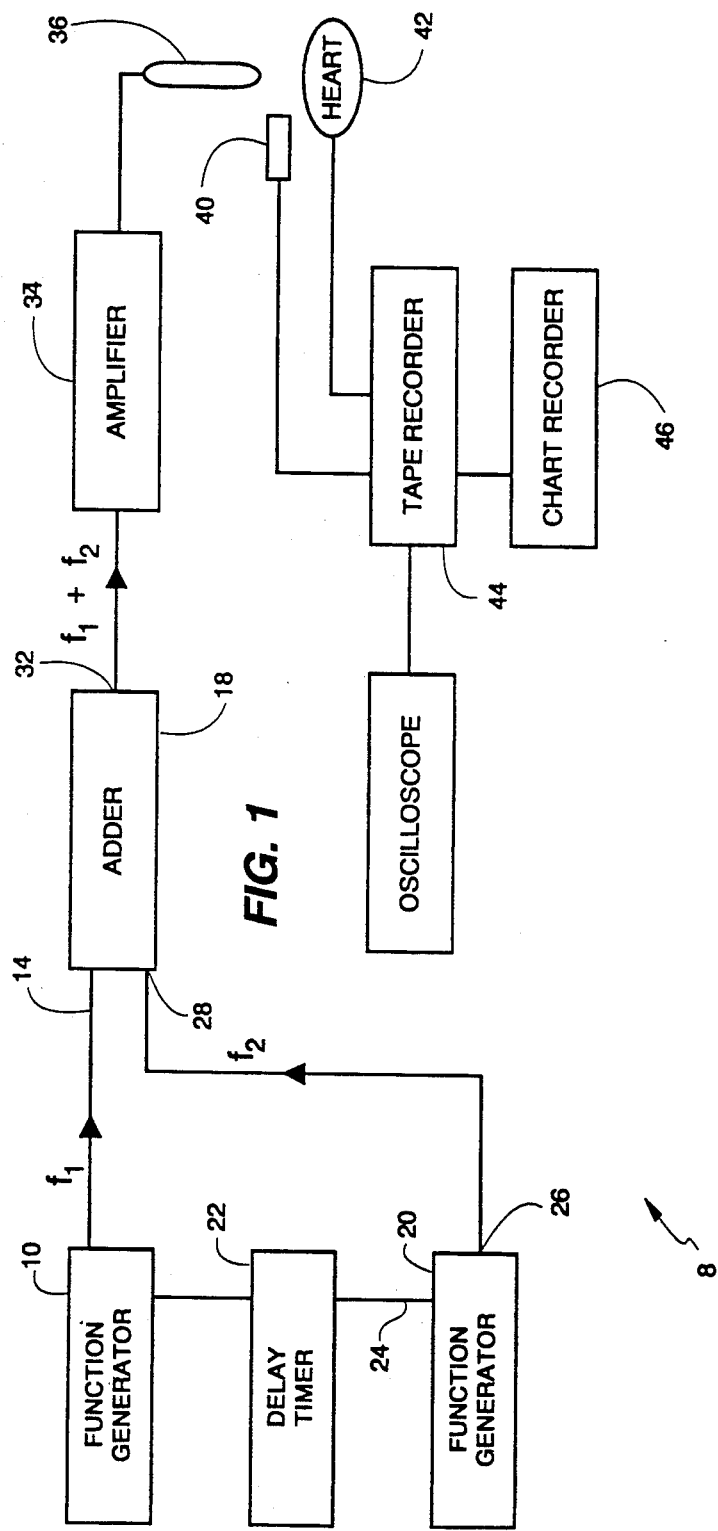
FIG. 1 is a schematic circuit diagram of the non-invasive magnetic pacemaker of the present invention.

The method of the present invention is designed and intended to control the heart rate of a person or animal by means of low intensity pulsed magnetic fields generated by a miniature coil inside a magnetic pacemaker device. The device itself can be either non-invasive, i.e., it is not implanted inside the body, or it can be used as a permanent pacemaker not using a lead system unlike devices using standard electric pulse stimulation of the heart. In the case of a non-invasive pacemaker it can be worn externally near the chest, such as in a shirt pocket or strapped to the body, and is powered by a small battery. In the case of a permanently implanted unit, the pulse generator can be inserted under the skin over the left chest, directing its beam to the heart and powered by standard power sources used with conventional pacemakers.

The invention is based on the operating principle of modifying cellular functions with low or medium intensity pulsed or modulated electromagnetic fields. Similar concepts have been used also for modification of cell growth. See C. Ramon et al.. "Inhibition of Growth Rate of Escherichia Coli by Extremely Low Frequency Weak Magnetic Fields," *Bioelectromaonetics*, 2:285-289 (1981); C. Ramon et al., "Electromagnetic Field Induced Growth Modulation of *B. subtilis* Bacteria," Fifth Annual Bioelectromagnetic Society Meeting, Jun. 12–16, 1983, University of Colorado, Boulder, Col. Both the wave shape and intensity of the pulse are important parameters in influencing the cellular functions of a cell.

It has been found that calcium uptake (which is responsible for many cellular functions requiring current flow) can be increased or decreased in isolated cells by magnetic field stimulation. S. M. Bawin and W. R. Adey, "Sensitivity of Calcium Binding in Cerebral Tissue to Weak Environmental Electric Fields Oscillating at Low Frequency," *Proc. Natl. Acad. Sci., USA.* 73:1999-2003 (1976). It should also be noted that behavioral responses and learning processes in animals can be modified in the presence of low frequency (0-20 Hz) modulated electromagnetic fields. Each type of cell, depending upon its shape and size, has its characteristic resonant frequencies. The surface charge densities of co-ions and counter-ions on the surface of the cell and in the fluid microenvironment in the vicinity of the cell, and the ionic current flow near and inside the cell can be greatly enhanced or decreased if a cell is exposed to an outside electromagnetic field at these resonant frequencies. See A. A. Pilla, "Electrochemical Information at Cell Surfaces and Junctions—Application to the Study and Manipulation of Cell Regulation" in H. Keyzer, F. Gutman (Eds.), *Biochemistry*, New York: Plenum Press, pp. 353-396 (1980); G. P. Drago et al., "The Frequency Dependence of an Analytical Model of an Electrically Stimulated Biological Structure," *Bioelectromaonetics*, 5:47-62 (1984).

These authors have emphasized that the ion flux across the cell membranes, counter-ion density, and the ion concentration in the vicinity of the cell membrane are frequency dependent quantities. In particular, the ion concentration more than doubles from the equilibrium value and the counter-ion density decreases five to seven times from the equilibrium value in the frequency range of 10-100 Hz. This would significantly modify the gating properties of the membrane's ionic channels, either by changing the "double-layer" effects of the membrane bound-divalent cations, or by changing the associations of the gating molecules in the membrane bilayer. Due to this modification of the properties of the ionic channels of the membrane, the gating or breakdown of the excitable cells will be observed in the presence of electromagnetic fields of frequencies below the relaxation frequency of 100 Hz.

Also, because of the electrical properties of the "double layer", the low-frequency electric field (less than 1 kHz) lines are heavily attenuated within the lipid bilayer or bend around it, but the magnetic field lines do not experience this type of attenuation or bending. Because of nonattenuation or nonbending, the magnetic field intensities required for the gating of the cardiac cells would be expected to be much lower than the intensities required for comparable electrical effects. A proper selection of waveshape, frequency, and repetition rate of the applied, low-intensity field are essential to observe such effects.

The electric field strength, which is related to the ionic charge density in the vicinity of the cell, may also be greatly modified. This, in turn, will facilitate the transfer of depolarization current from one cell to the next. This mechanism is more suitable for myocardial cells, where electrical transfer of excitation has been experimentally demonstrated, than in other types of cells such as skeletal muscle cells where a low-resistance connection between the cells is the primary requirement for an electrical excitation to propagate from one cell to the next.

The method and device of the present invention applies these concepts of cell membrane depolarization to control the heart rate due to the externally applied magnetic fields. The method uses low-to-medium-density pulsed magnetic fields. If one were to use only an electric field, however, it would have to be very strong, having potentially deleterious side effects, in order to penetrate deeper inside the body and obtain the same effect at the heart.

Magnetic field excitation of cardiac muscle can occur via indirect mechanisms as well as via direct depolarization. The indirect method of stimulation is a consequence of magnetic field augmentation of the sinoatrial node spontaneous discharge rate. This occurs because magnetic fields enhance automaticity or phase 4 cellular depolarization. Although this indirect means of cardiac excitation isn't as widely applicable as the direct depolarization effect of magnetic impulses, it does offer an alternative in select patients, for example those with isolated sinoatrial node dysfunction.

Regardless of whether magnetic field induced depolarization of the heart is directly or indirectly achieved, disclosed herein is a method of the present invention that is suitable for either purpose.

In the method of the present invention, magnetic pulses of special wave shape are generated by a miniature field coil located either outside the body, in the case of a transthoracic external pacemaker, or subcutaneously in the thoracic dermal tissues overlying the heart, in the case of a permanently implanted system. In this invention it has been found that magnetic pulses of specialized wave shapes at two or more fixed frequencies are usually required to modify cellular functions. Thus, a magnetic pulse at two mixed frequencies is used to excite the heart from outside the body. One magnetic pulse brings up the threshold of the cardiac cell membrane and the other discharges them.

FIG. 1 shows a schematic circuit diagram 8 of an embodiment of a magnetic pacemaker. The device includes a first function generator 10 which generates a first electrical signal having a predetermined waveform and frequency. In the systems tested to date, the wave has a biphasic sinusoidal shape with a frequency $f_1$ in the ranges of 0.1 Hz to 3000 Hz. This output signal is provided to one input 14 of an adder.

A second function generator 20 generates a second electrical signal also having a predetermined waveform and frequency. In the embodiments tested to date, the waveform of the signal generated by function generator 20 is a biphasic pulse having a sinusoidal, trapezoidal or triangular pulse shape and a frequency, $f_2$, in the ranges of 0.1 to 3000 Hz. The signal generated by function generator 20 is a pulsed signal having the aforementioned characteristics. In a typical added waveform, frequencies $f_1$ and $f_2$ could be same or different.

The frequency ranges of $f_1$ and $f_2$ given here are those which have been found to date to be of importance in affecting the heart rate.

A delay timer 22 is connected between the function generator 10 and the function generator 20. A trigger signal generated by the function generator 10 initiates the timer circuit 22 to generate a delayed trigger pulse which is fed to the input 24 of the function generator 20. Upon the appearance of each delayed trigger pulse at its input 24, the function generator 20 generates a pulsed signal having one of the aforementioned wave shapes at frequency $f_2$.

The output 26 of function generator 20 is fed to a second input 28 of the adder. The resultant added signal at the output 32 of the adder 18 has waveforms of the type shown in FIG. 2. The added biphasic output signal from the adder 18 is fed to a power amplifier 34 and then to a magnetic field coil 36.

Two coil design were used in these studies. A pair of circular coils in Helmholtz configuration was used for isolated-tissue experiments, and a cylindrical coil was used for the perfused rat-heart experiments and dog experiments. Each circular coil was 16 cm in diameter, 1.6 cm in width, and was made of 250 turns of 18-gauge insulated copper wire. The electrical parameters of each coil were: resistance, 2.6 ohms, and inductance, 15 mH. A variable capacitor was connected in parallel with the field coils for maximizing current in the capacitor-inductor loop. Axial separation between the coils was kept a 8 cm to maintain a uniform field. The coils were fixed, vertical and parallel to the surface of the tissue, so the field lines were perpendicular to the tissue's surface. This technique to produce uniform magnetic fields had been used earlier in bacterial culture experiments.

The cylindrical coil used in our experiments was 15 cm long, with an external diameter of 2.54 cm. Its soft-iron core was 1.27 cm in diameter. The electrical parameters were: resistance, 2.41 ohms, inductance, 77.8 mH, and number of turns, 1070.

Figure 2:
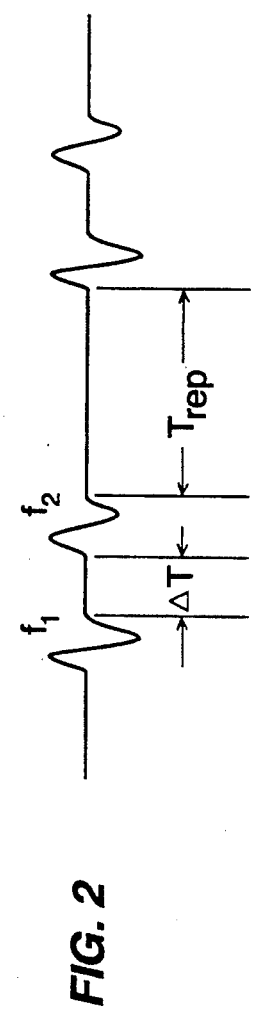
FIG. 2 is a graph of a waveform generated by the circuit 5 of FIG. 1.

Referring now to FIG. 2, $T_{rep}$ is a repetition time interval between successive sets of added frequency pulses. $T_{rep}$ usually is very close to the interval between the successive heart beats. For humans, $T_{rep}$ is in the range of 0.2 to 1 second. $\Delta T$ represents a time interval delay time between pulses of frequencies $f_1$ and $f_2$, and it is usually in the range of 0 to 200 msec.

Data collection was accomplished by using a magnetic sensor 40 and an electrode 42 to obtain an ECG. These data were then stored on an 8 track magnetic tape recorder 44 and viewed on a chart recorder 46. Six experiments were performed on magnetic stimulation of atrial tissue excised from dogs' hearts, e.g. heart 43 in FIG. 1. In a typical experiment the experimental arrangements were as follows:

The atrial tissue was excised from a dog heart and placed in a circulating bath of Tyrode's solution at 37° C. and oxygenated with 95% oxygen and 5% dioxide. [J. R. Neeley et al., "Effect of ischemia on function and metabolism of the isolated working rat heart," *American Journal of Physiology*, 225: 651-658 (1973).] Under these conditions the tissue remained viable for up to six hours. In these experiments and those described below for the isolated rat heart, the ECG was obtained using very high impedance, 20 cm long, glass-KCl electrodes to eliminate electric field-induced stimulation.

Figure 3:
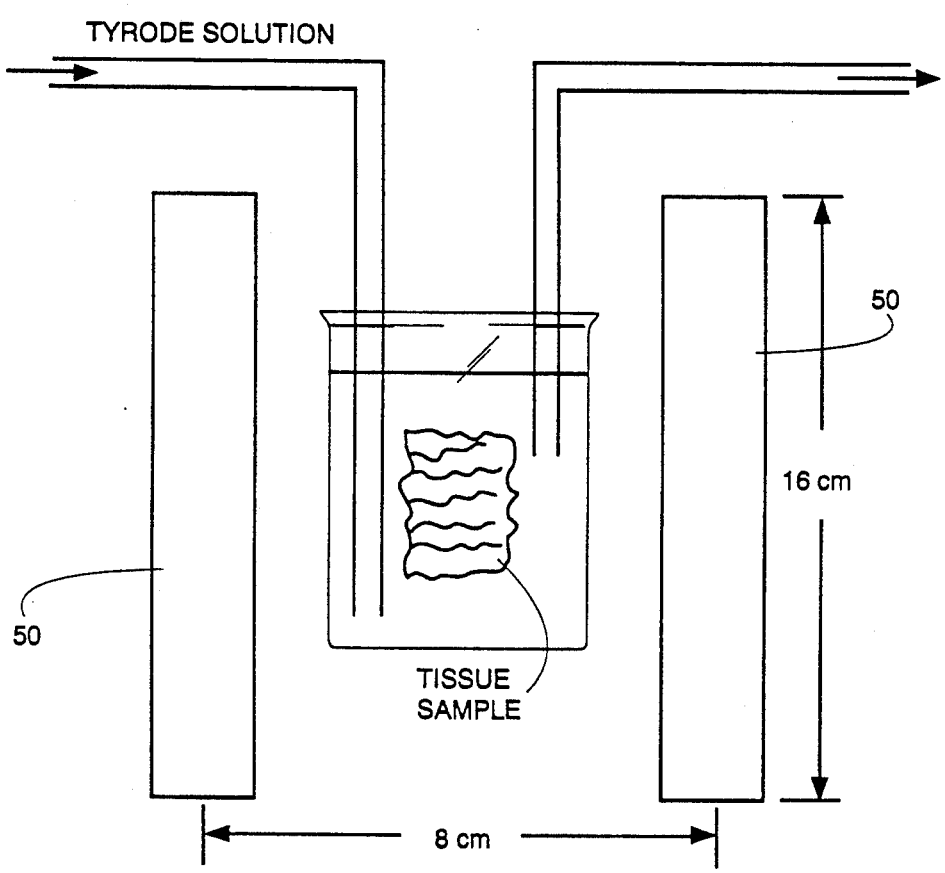
FIG. 3 is a schematic diagram of the arrangement of atrial tissue from a dog heart in a magnetic field.

The tissue was placed between two circular coils 50 in the Helmholtz configuration one of which is shown in FIG. 3. The electrical parameters of these coils 50 were: inductance (L)=15 mH; resistance (R)=2.6 ohms; and number of turns (N)=330. Each coil was 16 cm outside diameter. The conditions examined included: $f_1$ in the range of 0.1 to 100 Hz; $f_2$ in the range of 0.1 to 100 Hz; $\Delta T$ in the range of 0 to 100 mSec; and B in the range of 10 to 200 gauss.

Optimum conditions for magnetic pacing of the dog atrial tissue were found to be, $f_1=4.5$ Hz; $f_2=6$ Hz; $\Delta T=30$ mSec; and B=75 to 100 gauss. It was also discovered that single pulses do not work: rather a pulse train of 2 to 3 pulses resulted in triggering of the heart rate of the tissue.

Figure 4:
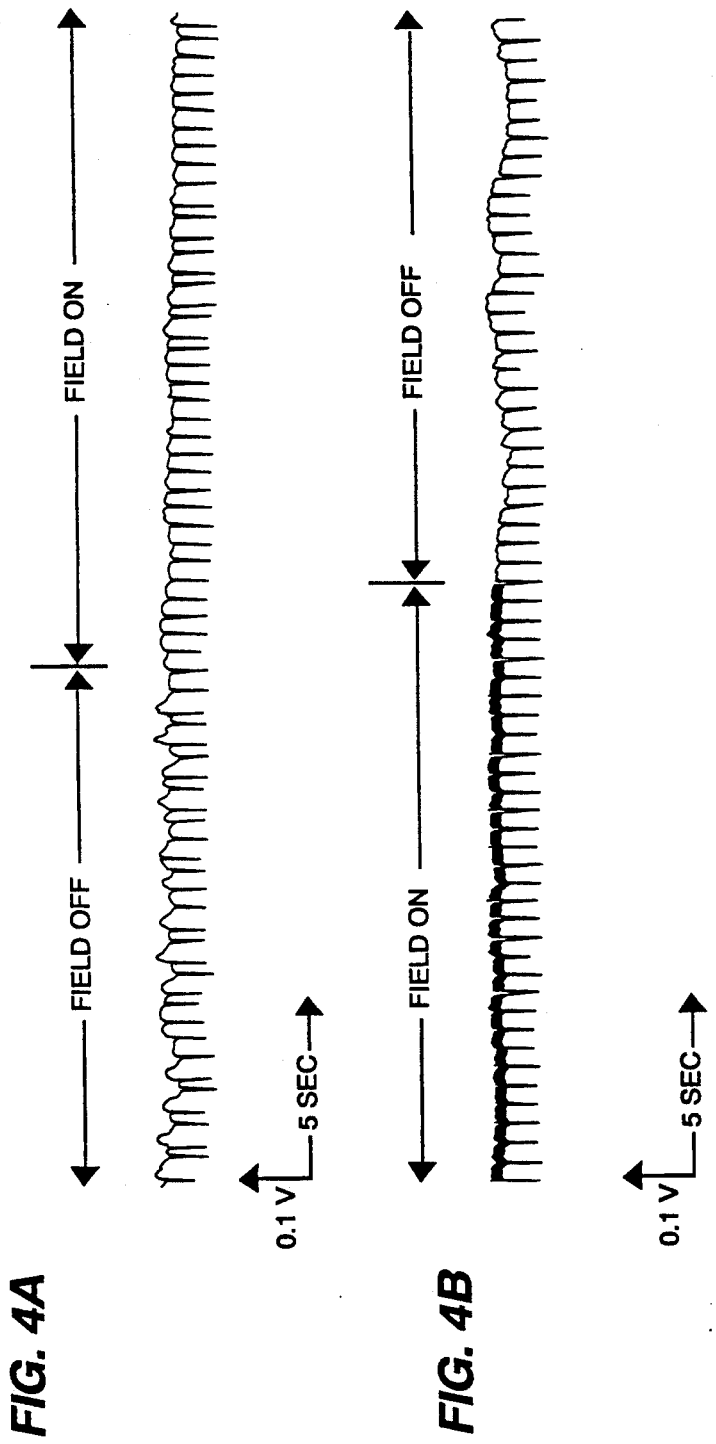
FIGS. 4A and B show the ECG from the atrial tissue of the dog heart.

FIG. 4 shows the details of the magnetic pacing of the ECG from the atrium of the dog heart and shows that when the field was operating, the cardiac rhythm became regular as contrasted to the irregularity existing in the absence of the magnetic field.

We performed an experiment also using a whole dog model, the data recorded on magnetic tape and strip chart included: ECG, blood flow (indwelling catheter), $f_1$, $f_1+f_2$, demand pacing signal, magnetic pulse shape, current, and respiration. A cylindrical coil was utilized to generate the magnetic fields.

Conditions examined included varying $f_1$ from 0 to 50 Hz, $f_2$ from 0 to 100 Hz, $T_3$ from 4 to 200 mSec, and B from 50 to 500 gauss.

Figure 5:
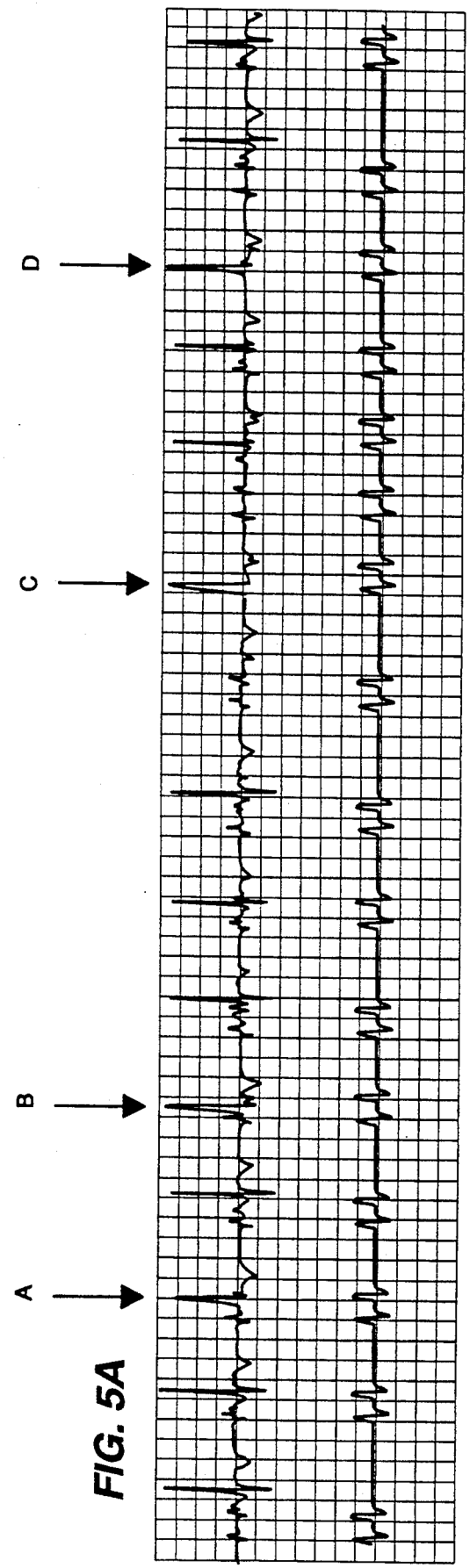
FIG. 5A shows the ECG of a dog heart when exposed to magnetic field pulses of 9 Hz frequency as shown in FIG. 5B.

FIG. 5A is a graph of heart beats and FIG. 5B is a graph of magnetic field pulses. The arrows A-D indicate where the heart beat is excited by the magnetic field pulses.

The conditions for the cardiac pacing illustrated in FIGS. 6A and 6B included $f_1=9$ Hz; $f_2=9$ Hz; $\Delta T=50$ mSec; and B=200 gauss.

Figure 6:
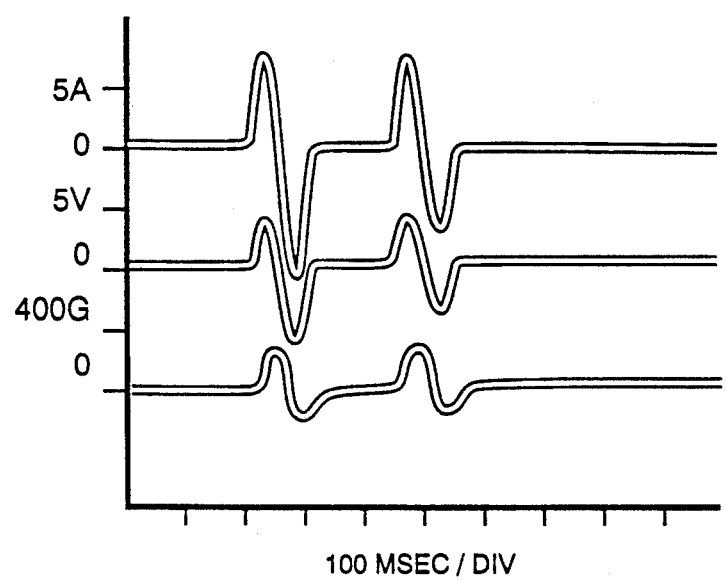
FIG. 6 shows oscilloscope traces of current, voltage and magnetic field of the electromagnetic parameters associated with dog heart referred to in FIG. 5.

FIG. 6 is a representation of the oscilloscope showing details of voltage wave shapes of $f_1+f_2$, current waveform, and the pulse shape of the magnetic field as monitored by use of a magnetic field detector.

In another experiment, whole rat hearts were excised from anesthetized rats and placed in a perfusion apparatus in which the heart was not only perfused with oxygenated Tyrode's solution at 37° C. through a major artery, but was also bathed with the same solution to prevent desiccation and to facilitate maintenance of temperature. This type of system is commonly known as the Langendorf preparation. It is normally employed for physiological studies of excised whole hearts. Glass electrodes as described above were used to avoid electrical stimulation of the heart. The ECG and flow were monitored on a storage oscilloscope and recorded on a chart recorder.

Magnetic fields were generated by the previously described Helmholtz coils 50. Parameters examined included: $f_1$ in the range of 1 to 200 Hz; $f_2$, in the range of 1 to 200 Hz; $\Delta T$, in the range of 0 to 100 mSec; and B, in the range of 10 to 200 gauss.

Two frequency ranges were found in which the rat heart responded well to the outside magnetic fields. These frequency ranges were: a) 20-25 Hz, and b) 40-55 Hz. Beyond these two frequency ranges the magnetic fields either did not affect the natural rhythm of the heart or caused it to go into dysrhythmia.

Figure 7A:
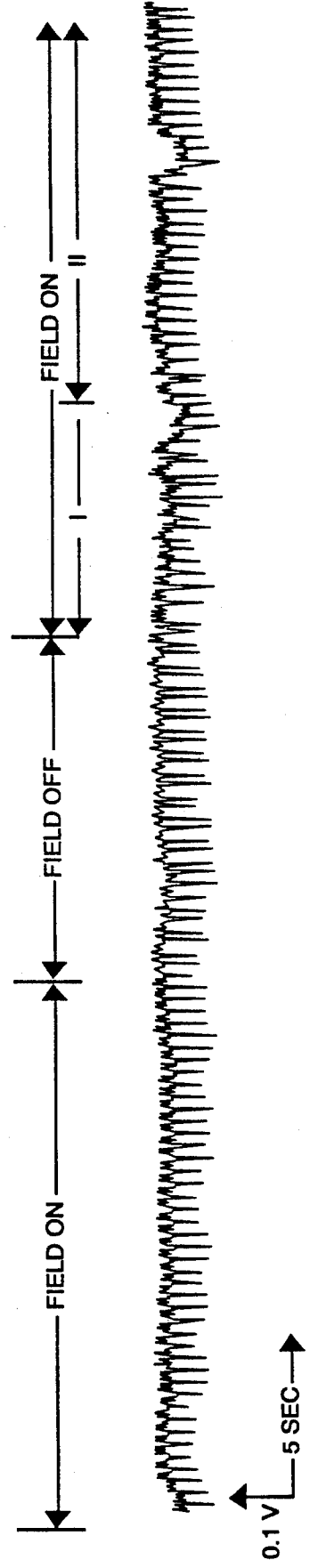
FIGS. 7A and 7B show the ECG of an isolated rat heart.

FIGS. 7A and B show the ECG data from the isolated rat heart. FIG. 7A shows that heart beat becomes erratic when the field is turned off. When the field is turned on again at a different frequency and the frequency was varied to show that at the proper frequency the magnetic pulses locked on to the heart beat to make it regular.

Figure 7B:
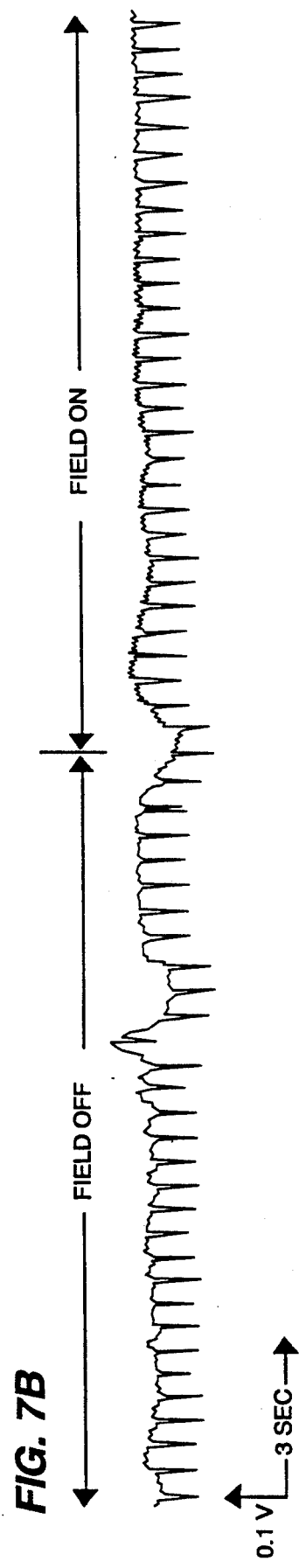

FIG. 7B shows that when the natural beating of the heart was erratic, the application of the magnetic field of the above described frequency ranges resulted in a return to a regular rhythm.

Also, an increase in heart rate can be controlled by changing the repetition rate of the applied magnetic field. The heart rate can be increased, for example, from 170 beats/min to 180 beats/min by applying the magnetic field. The best pacing conditions were obtained with the following parameters: $f_1=20-25$ and 40-55 Hz;

$f_2 = 20$–$25$ and $40$–$55$ Hz, $T_3 = 10$–$50$ mSec, and $B = 50$–$100$ gauss.

To summarize, in all of the animal models examined cardiac pacing was observed. The exact conditions for successful pacing varied among species. Two frequencies, $f_1$ and $f_2$, separated by species dependent intervals, $\Delta T$, were essential in all cases. The first frequency, $f_1$, is apparently necessary to "arm" the cardiac cells and the second frequency, $f_2$, appears necessary to "trigger" the depolarization of the cells. Irregular natural cardiac pacing can be controlled in the presence of the specific magnetic fields while the rate of pacing can be increased at least 20% by modifying the triggering of the magnetic pulses.

The entire circuit, including a battery power source (not shown) and the coil 36, can be contained in a casing that is substantially transparent to the magnetic field generated by the coil. The casing may, for example, be made of plastic or any other suitable material that permits the magnetic field to pass essentially unrestricted into the body for controlling the heart muscle.

The pacemaker device and method of the present invention may be embodied in other specific forms without departing from the teachings or essential characteristics of the invention. The described embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A cardiac pacemaker for controlling heart rate comprising:
   first function generating means for generating a first electrical signal having a first wave shape and a first frequency;
   second function generating means for generating a second electrical signal having a second wave shape and a second frequency;
   delay timer means coupled between said first and second function generators for triggering said second function generator as a delayed function of a trigger signal generated by said first function generator;
   adder means coupled to said first and second function generating means for adding said first and second electrical signals;
   field coil means coupled to the output of said adder means for generating pulsed magnetic field signals as a function of said added first and second electrical signals; and
   a housing containing said first and second function generating means, said adder means, and said field coil means, said housing comprising, at least partially, magnetically transparent material, said housing being adapted to be located externally or subcutaneously near the hear to thereby control heart rate as a function of said pulsed magnetic field signals.

2. The cardiac pacemaker of claim 1, wherein said adder means includes means to provide biphasic pulses at the output of said adder means.

3. The cardiac pacemaker of claim 1, wherein said first function generator comprises means for generating a first signal having a frequency $f_1$ in the range of 0.1 Hz to 3000 Hz.

4. The cardiac pacemaker of claim 3, wherein said first function generator includes means to generate a biphasic pulse signal.

5. The cardiac pacemaker of claim 3, wherein said first function generator includes means to generate a sinusoidal pulse signal.

6. The cardiac pacemaker of claim 3, wherein said first function generator includes means to generate triangular pulses at its output.

7. The cardiac pacemaker of claim 1, wherein said second function generator comprises means for generating a second signal having a frequency $f_2$ in the range of 0.1 Hz to 3000 Hz.

8. The cardiac pacemaker of claim 4, wherein said second function generator includes means to generate biphasic pulse signals at its output.

9. The cardiac pacemaker of claim 7, wherein said second function generator includes means to generate trapezoidal pulses at its output.

10. The cardiac pacemaker of claim 7, wherein said second function generator includes means to generate triangular pulses at its output.

11. The cardiac pacemaker of claim 10, wherein said field coil means comprises means for generating a magnetic field having a field strength of not more than about 200 gauss.

12. The cardiac pacemaker of claim 11, wherein said field coil means comprises means for generating a magnetic field having a field strength of not more than about 10 guass and not less than 0.5 guass.

13. A method of controlling heart rate without the use of endocardial leads comprising the steps of:
    generating a first electrical signal having a first wave shape and a first frequency;
    generating a second electrical signal having a second wave shape and a second frequency;
    triggering said second electrical signal as a delayed function of a trigger signal corresponding to said first electrical signal;
    adding said first and second electrical signals;
    generating pulsed magnetic field signals as a function of said added first and second electrical signals; and
    transmitting said pulsed magnetic field signals from position extrinsic to the chest or subcutaneously over the heart into the chest to thereby control the heart rate of the animal or human as a function of said pulsed magnetic field signals.

14. The method for controlling heart rate of claim 13, further comprising the step of generating biphasic pulsed magnetic field signals having components comprising at least one of sinusoidal, trapezoidal, biphasic and triangular pulses.

15. The method for controlling heart rate of claim 13, wherein said first electrical signal has a frequency $f_1$ in the range of 0.1 Hz to 3000 Hz.

16. The method for controlling heart rate of claim 13, wherein said second electrical signal has a frequency $f_2$ in the range of 0.1 to 3000 Hz.

17. The method for controlling heart rate of claim 13, wherein said pulsed magnetic field signals have a field strength of not more than about 200 gauss.

18. The method for controlling heart rate of claim 13, wherein said pulsed magnetic field signals have a field strength of not more than about 10 gauss and not less than 0.5 gauss.

19. A cardiac pacemaker for controlling heart rate comprising:

means for generating first and second electrical signals having selected wave shapes selected from the group consisting of sinusoidal, triangular, trapezoidal and biphasic waveforms in the frequency range of 0.1 Hz to 3000 Hz;

delay timer means coupled between said first and second generating means for triggering said second generator means as a delayed function of a trigger signal generated by said first generator means;

means for adding said first and second signals;

means for supplying the sum of said first and second signals to magnetic field generating means for generating magnetic fields corresponding to said sum of said first and second signals; and means for applying said magnetic fields to a heart for controlling heart rate as a function of said magnetic fields.

20. A cardiac pacemaker for controlling heart rate comprising means for generating at least first and second magnetic field pulses; delay timer means coupled between said first and second generating means for triggering said second generator means as a delayed function of a trigger signal generated by said first generator means; and means for applying said first and second magnetic field pulses sequentially to a heart with the first pulse bringing the cardiac cells in the heart close to the threshold of depolarization and said second following, or second and subsequent following, pulses bringing the cardiac cells to the point of firing to depolarization.

21. A method for controlling heart rate comprising the steps of:

generating first and second electrical signals having selected wave shapes selected from the group consisting of sinusoidal, triangular, trapezoidal and biphasic waveforms and variations thereof in the frequency range of 0.1 Hz to 3000 Hz;

triggering said second electrical signal as a delayed function of a trigger signal corresponding to said first electrical signal;

adding said first and second signals;

supplying the sum of said first and second signals to magnetic field generating means;

generating magnetic fields corresponding to said sum of said first and second signals; and applying said magnetic fields to a heart for controlling heart rate as a function of said magnetic fields.

22. A method for controlling heart rate comprising the steps of:

generating at least first and second magnetic field pulses;

triggering said second electrical signal as a delayed function of a trigger signal corresponding to said first electrical signal;

applying said first and second magnetic field pulses sequentially to a heart;

bringing the cardiac cells in the heart close to the threshold of depolarization with said first pulse; and bringing the cardiac cells to the point of firing to depolarization with said second following, or second and subsequent following, pulses.

* * * * *

UNITED STATES PATENT AND TRADEMARK OFFICE
CERTIFICATE OF CORRECTION

PATENT NO. : 5,170,784
DATED : December 15, 1992
INVENTOR(S) : Ceon Ramon and Gust H. Bardy It is certified that error appears in the above-indentified patent and that said Letters Patent is hereby corrected as shown below:

Column 7, line 59 "near the hear" should be --near the heart--

Column 8, line 14 "of claim 4" should be --of claim 7--

Column 8, line 24 "of claim 10" should be --of claim 1--

Signed and Sealed this

Twenty-second Day of March, 1994

Attest:

BRUCE LEHMAN

*Attesting Officer*    *Commissioner of Patents and Trademarks*